United States Patent [19]

Davis et al.

[11] 4,396,770

[45] Aug. 2, 1983

[54] 1-[3-(6-FLUORO-1,2-BENZISOXAZOL-3-yl)PROPYL]-4-HYDROXY-4-PHENYL-PIPERIDINES

[75] Inventors: Larry Davis, Sergeantsville; Joseph T. Klein, Somerville, both of N.J.

[73] Assignee: Hoechst-Roussel Pharmaceuticals Inc., Somerville, N.J.

[21] Appl. No.: 366,247

[22] Filed: Apr. 9, 1982

[51] Int. Cl.$^3$ .............................................. C07D 413/06
[52] U.S. Cl. .................................... 546/198; 424/267; 546/217; 548/241
[58] Field of Search ........................................ 546/198

[56] References Cited

U.S. PATENT DOCUMENTS 3,951,999  4/1976  Saunders et al. ..................... 548/241
4,235,914  11/1980  Sasajima et al. ..................... 424/267

FOREIGN PATENT DOCUMENTS 40639 12/1981 European Pat. Off. .
4970963 11/1972 Japan .
51-136666 11/1976 Japan .

OTHER PUBLICATIONS

Uno, H., et al., *Chem. Pharm. Bull.* (Japan), 24, 632 (1976).
*Chemical Abstracts*, 87: 39459c (1977) [Uno et al., Japan, Kokai 76,136,666 11/26/76].
Janssen, P., *Int. J. Neuropharmacol.*, 1962, 1, 145–148.]

Primary Examiner—Richard A. Schwartz
Attorney, Agent, or Firm—Raymond R. Wittekind

[57] ABSTRACT

Novel 1-[3-(6-fluoro-1,2-benzisoxazol-3-yl)propyl]-4-hydroxy-4-phenylpiperidines, processes for the preparation thereof, and methods of treating psychoses and alleviating pain employing compounds and compositions thereof are disclosed.

14 Claims, No Drawings

1-[3-(6-FLUORO-1,2-BENZISOXAZOL-3-YL)PROPYL]-4-HYDROXY-4-PHENYLPIPERIDINES

DESCRIPTION OF THE INVENTION

The present invention relates to novel 1-[3-(1,2-benzisoxazol-3-yl)propyl]-4-hydroxy-4-phenylpiperidines. More particularly, the present invention relates to 1-[3-(6-fluoro-1,2-benzisoxazol-3-yl)propyl]-4-phenyl-4-hydroxypiperidines of formula 1,

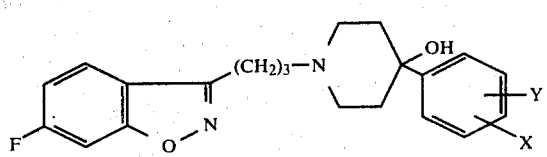

wherein X is hydrogen, loweralkyl, loweralkoxy, halogen or trifluoromethyl; Y is hydrogen or trifluoromethyl with the proviso that Y is hydrogen when X is hydrogen, loweralkyl, loweralkoxy or trifluoromethyl and Y is hydrogen or trifluoromethyl when X is halogen; the optical antipodes thereof, or pharmaceutically acceptable addition salts thereof, which are useful for treating psychoses and alleviating pain, alone or in combination with inert psychoses treating and pain alleviating adjuvants.

Preferred 1-[3-(1,2-benzisoxazol-3-yl)propyl]-4-hydroxy-4-phenylpiperidines are those wherein X is halogen and Y is hydrogen. Most preferred are those wherein the halogen is bound to the 4-position of the benzene ring.

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "halogen" refers to a member of a family consisting of chlorine, fluorine, bromine or iodine. The term "lower" as applied to any of the aforementioned groups refers to a group having a carbon skeleton containing up to and including 5 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof. The formulas of the compounds shown herein are intended to encompass all possible optical isomers of the compounds so depicted.

The novel 1-[3-(6-fluoro-1,2-benzisoxazol-3-yl)propyl]-4-hydroxy-4-phenylpiperidines of formula 1, the compounds of the present invention, are prepared by condensing a Grignard reagent of formula 2

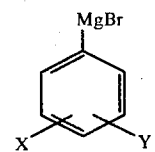

wherein X and Y are as before, prepared by conventional method from a bromobenzene of formula 3

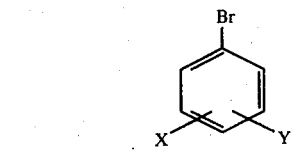

wherein X and Y are as before with magnesium (see, for example, M. S. Kharasch, "Grignard Reactions of Nonmetallic Substances", Prentice Hall, New York, 1954, Chapter II), with 1-[3-(6-fluoro-1,2-benzisoxazol-3-yl)propyl]-4-piperidone of formula 4

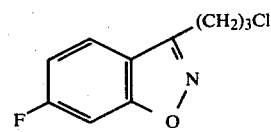

the synthesis of which is described in U.S. patent application Ser. No. 366,245 filed Apr. 9, 1982. The condensation is conveniently performed by treating the piperidone 4 with the Grignard reagent 2 in a suitable solvent. Among suitable solvents there may be mentioned ethereal solvents such as, for example, diethyl ether, dimethoxyethane, dimethoxyethoxyethane, dioxane, tetrahydropyran and tetrahydrofuran. Tetrahydrofuran is preferred.

The condensation temperature is not narrowly critical. It is desirable, however, to conduct the condensation at a temperature within the range of about −10° C. to about 40° C. to assure a reasonable rate of conversion. A condensation temperature of about ambient temperature is preferred.

Alternatively, the compounds of the present invention, the 1-[3-(6-fluoro-1,2-benzisoxazol-3-yl)propyl]-4-hydroxy-4-phenylpiperidines of formula 1, are prepared by condensing 3-(3-chloropropyl)-6-fluoro-1,2-benzisoxazole of formula 5 the synthesis of which is described in U.S. patent application Ser. No. 257,698, filed Apr. 27, 1981, was readily available 4-hydroxy-4-phenylpiperidines of formula 6

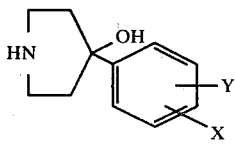

wherein X and Y are as above. The condensation is conveniently performed by treating the halide 5 with the piperidine 6 in the presence of an acid acceptor, a displacement promotor and a suitable solvent. Among acid acceptors, there may be mentioned alkali metal carbonates and alkali metal bicarbonates such as, for example, lithium carbonate, sodium carbonate and potassium carbonate, and lithium bicarbonate, sodium bicarbonate and potassium bicarbonate. Potassium carbonate and sodium bicarbonate are preferred. Among displacement promotors, there may be mentioned alkali metal halides such as, for example, sodium iodide and potassium iodide, and sodium bromide and potassium bromide. Potassium iodide is preferred. Among suitable solvents, there may be mentioned polar aprotic substances such as, for example, dimethylformamide, dimethylacetamide and hexamethylphosphoramide. Dimethylformamide is preferred. The temperature at which the condensation is conducted is not narrowly critical. It is desirable, however, to perform the condensation at a temperature within the range of about 50° C. to about 130° C. to assure a reasonable rate of conversion. A reaction temperature within the range of about 70° C. to 110° C. is preferred.

The 1-[3-(6-fluoro-1,2-benzisoxazol-3-yl)propyl]-4-hydroxy-4-phenylpiperidines of the present invention are useful as analgesic agents due to their ability to alleviate pain in mammals which is demonstrated in the phenyl-para-quinone writhing assay in mice, a standard assay for analgesia [Proc. Soc. Exptl. Biol. Med., 95, 729 (1953)]. Presented in Table 1 is the analgesic activity of representative compounds of the invention and two standards, expressed as the estimated subcutaneous dose at which the mice experience a 50% reduction in phenyl-para-quinone induced writhes, i.e., the $ED_{50}$-value.

TABLE 1

| Compound | Analgesic Activity ($ED_{50}$ mg/kg) |
| --- | --- |
| 1-[3-(6-Fluoro-1,2-benzisoxazol-3-yl)propyl]-4-hydroxy-4-phenyl-piperidine | 5.9 |
| 1-[3-(6-Fluoro-1,2-benzisoxazol-3-yl)propyl]-4-(3-chlorophenyl)-4-hydroxypiperidine hydrochloride | 0.8 |
| 1-[3-(6-Fluoro-1,2-benzisoxazol-3-yl)propyl]-4-hydroxy-4-(4-methoxyphenyl)piperidine hydrochloride | 3.8 |
| 1-[3-(6-Fluoro-1,2-benzisoxazol-3-yl)propyl]-4-(4-fluorophenyl)-4-hydroxypiperidine | 6.2 |
| 1-[3-(6-Fluoro-1,2-benzisoxazol-3-yl)propyl]-4-hydroxy-4-(3-trifluoromethylphenyl)piperidine hydrochloride | 1.0 |
| propoxyphene (standard) | 3.9 |
| pentazocin (standard) | 1.3 |

Analgesia production is achieved when the present 1-[3-(6-fluoro-1,2-benzisoxazol-3-yl)propyl]-4-hydroxy-4-phenylpiperidines are administered to a subject requiring such treatment as an effective oral, parenteral or intravenous dose of from 0.01 to 50 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 1-[3-(6-fluoro-1,2-benzisoxazol-3-yl)propyl]-4-hydroxy-4-phenylpiperidines of the present invention are useful for treating psychoses by virtue of their ability to block apomorphine-induced climbing in mammals.

Antipsychotic activity is determined in the climbing mice assay by a method similar to those described by P. Protais et al., Psychopharmacol., 50, 1 (1976) and B. Costall, Eur. J. Pharmacol., 50, 39 (1978).

The subject CK-1 male mice (23–27 grams) are group-housed under standard laboratory conditions. The mice are individually placed in wire mesh stick cages (4"×4"×10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
| --- | --- |
| Mice with: | |
| 4 paws on bottom (no climbing) | 0 |
| 2 paws on wall (rearing) | 1 |
| 4 paws on the wall (full climbing) | 2 |

Mice consistently climbing before the injection of apomorphine will be discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally—apomorphine subcutaneously) is set to 100%. $ED_{50}$ values with 95% confidence limits are calculated by a Linear Regression Analysis. Antipsychotic activity expressed as the $ED_{50}$ value of representative 1-[3-(6-fluoro-1,2-benzisoxazol-3-yl)propyl]-4-hydroxy-4-phenylpiperidines as well as two standard antipsychotics are presented in Table II.

TABLE II

| Compound | Antipsychotic Activity $ED_{50}$ (mg/kg) |
| --- | --- |
| 4-(4-chlorophenyl)-1-[3-(6-fluoro-1,2-benzisoxazol-3-yl)propyl]-4-hydroxypiperidine | 0.51 |
| 1-[3-(6-fluoro-1,2-benzisoxazol-3-yl)propyl]-4-hydroxy-4-phenyl-piperidine | 9.6 |
| 1-[3-(6-fluoro-1,2-benzisoxazol-3-yl)propyl]-4-hydroxy-4-(4-tolyl)-piperidine | 0.56 |

TABLE II-continued

| Compound | Antipsychotic Activity ED$_{50}$ (mg/kg) |
| --- | --- |
| 1-[3-(6-fluoro-1,2-benzisoxazol-3-yl)propyl]-4-hydroxy-4-(4-trifluoromethylphenyl)piperidine | 3.1 |
| 1-[3-(6-fluoro-1,2-benzisoxazol-3-yl)propyl]-4-(3-chlorophenyl)-4-hydroxypiperidine hydrochloride | 0.8 |
| 1-[3-(6-fluoro-1,2-benzisoxazol-3-yl)propyl]-4-(4-fluorophenyl)-4-hydroxypiperidine | 0.8 |
| 1-[3-(6-fluoro-1,2-benzisoxazol-3-yl)propyl]-4-hydroxy-4-(3-trifluoromethylphenyl)piperidine hydrochloride | 0.25 |
| 1-[3-(6-fluoro-1,2-benzisoxazol-3-yl)propyl]-4-hydroxy-4-(2-methylphenyl)piperidine hydrochloride | 8.3 |
| haloperidol (standard) | 0.11 |
| sulpiride (standard) | 4.5 |

Antipsychotic activity is achieved when the present 1-[3-(6-fluoro-1,2-benzisoxazol-3-yl)propyl]-4-hydroxy-4-phenylpiperidines are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not, to any extent, limit the scope or practice of the invention.

Effective amounts of the compounds of the invention may be administered to a subject by any one of various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1-[3-(6-Fluoro-1,2-benzisoxazol-3-yl)propyl]-4-hydroxy-4-phenylpiperidine

To 50 ml of dry dimethylformamide was added, 6.0 g of 4-hydroxy-4-phenylpiperidine, 8.0 g of 3-(3-chloropropyl)-6-fluoro-1,2-benzisoxazole, 13.0 g of sodium bicarbonate, and a few crystals of potassium iodide. After stirring at 80° C. for one hr, the mixture was cooled, filtered, and the filtrate evaporated to an oil. The oil was stirred with 100 ml water for five mins, and then extracted with ether/ethyl acetate. The organic layer was washed with water (2×), saturated sodium chloride solution and dried over anhydrous magnesium sulfate. After filtering, the solvents were evaporated. Trituration with ether gave 3.0 g (25%) of product, mp 133°–137° C. Recrystallization twice from ethyl ether gave the analytical sample, mp 138°–139° C.

Analysis

Calculated for $C_{21}H_{23}FN_2O_2$: 71.16%C, 6.54%H, 7.91%N. Found: 71.34%C, 6.51%H, 7.66%N.

EXAMPLE 2

4-(3-Chlorophenyl)-1-[3-(6-fluoro-1,2-benzisoxazol-3-yl)propyl]-4-hydroxypiperidine hydrochloride To a suspension of 1.2 g of magnesium shavings and a few drops of dibromoethane in 30 ml of ether was added a solution of 8.7 g of 3-bromochlorobenzene in 20 ml of ether at such a rate so as to maintain reflux. After the addition was complete, the mixture was diluted with 30 ml of tetrahydrofuran and then a solution of 6.3 g of 1-[3-(6-fluoro-1,2-benzisoxazol-3-yl)propyl]-4-piperidone in 30 ml of tetrahydrofuran was slowly added. After one hr, the mixture was diluted with ether, poured into 400 ml of saturated ammonium chloride solution and extracted with ether. The organic extracts were washed with water (2×), saturated sodium chloride solution and dried over anhydrous magnesium sulfate, filtered and concentrated to an oil. The oil was converted to 8.5 g (88%) of product, mp 170°–172° C., by treatment with ethereal hydrogen chloride. An analytical sample was obtained by recrystallization from ethyl acetate/methanol and had, mp 188°–189° C.

Analysis

Calculated for $C_{21}H_{22}ClFN_2O_2.HCl$: 59.30%C, 5.45%H. Found: 59.52%C, 5.56%H.

EXAMPLE 3

4-(4-Chlorophenyl)-1-[3-(6-fluoro-1,2-benzisoxazol-3-yl)propyl]-4-hydroxypiperidine To 30 ml of dry dimethylformamide was added 3.0 g of 4-(4-chlorophenyl)-4-hydroxypiperidine, 2.99 g of 3-(3-chloropropyl)-6-fluoro-1,2-benzisoxazole, 8.0 g of sodium bicarbonate, and a crystal of potassium iodide. After stirring at 90° C. for one hr, the mixture was evaporated to an oil. The oil was stirred with 100 ml of water for five mins, and then extracted with ether. The ether solution was washed with water (2×), saturated sodium chloride solution and dried over anhydrous magnesium sulfate. After filtering, the solvent was evaporated. Recrystallization of the residue from ethyl ether gave 3.6 g of product, mp 142°–145° C. The analytical sample was obtained by recrystallization from ethyl ether and had mp 148°–150° C.

Analysis

Calculated for $C_{21}H_{22}ClFN_2O_2$: 64.86%C, 5.70%H, 7.21%N. Found: 64.75%C, 5.64%H, 7.15%N.

EXAMPLE 4

1-[3-(6-Fluoro-1,2-benzisoxazol-3-yl)propyl]-4-(4-fluorophenyl)-4-hydroxypiperidine To a suspension of 1.1 g of magnesium shavings and a few drops of dibromoethane in 30 ml of ether was added a solution of 7.9 g of p-bromofluorobenzene in 20 ml of ether at a rate to maintain reflux of the mixture. After the addition was complete, the mixture was slowly diluted with 30 ml of tetrahydrofuran and then a solution of 5 g of 1-[3-(6-fluoro-1,2-benzisoxazol-3-yl)propyl]-4-piperidone in 30 ml of tetrahydrofuran was slowly added. After one hr, the mixture was diluted with ether, poured into 400 ml of saturated ammonium chloride solution and extracted with ether. The organic extracts were washed with water (2×), saturated sodium chloride solution and dried over anhydrous magnesium sulfate, filtered and concentrated. The residue was recrystallized from hexanes/ether to give 3.6 g (54%) of product, mp 100°–101° C.

Analysis

Calculated for $C_{21}H_{22}F_2N_2O_2$: 67.72%C, 5.95%H. Found: 67.88%C, 5.67%H.

EXAMPLE 5

1-[3-(6-Fluoro-1,2-benzisoxazol-3-yl)propyl]-4-hydroxy-4-(2-methylphenyl)piperidine hydrochloride To a suspension of 0.9 g of magnesium shavings and a few drops of dibromoethane in 30 ml of ether was added a solution of 6.2 g of 2-bromotoluene in 30 ml of water. After the addition was complete, the mixture was stirred under reflux for one hr, cooled, and a solution of 5 g of 1-[3-(6-fluoro-1,2-benzisoxazol-3-yl)propyl]-4-piperidone in 50 ml of tetrahydrofuran was added. After one hr, the mixture was diluted with ether, poured into 400 ml of saturated ammonium chloride solution and extracted with ether. The organic extracts were washed with water (2×), saturated sodium chloride solution and dried over anhydrous magnesium sulfate, filtered and concentrated. The residue was converted to 6.4 g (82%) of product by treatment with ethereal hydrogen chloride. Recrystallization from ethyl acetate/methanol gave the analytical sample, mp 191°–192° C. (dec).

Analysis

Calculated for $C_{22}H_{25}FN_2O_2.HCl$: 65.26%C, 6.47%H. Found: 65.14%C, 6.62%H.

EXAMPLE 6

1-[3-(6-Fluoro-1,2-benzisoxazol-3-yl)propyl]-4-(4-tolyl-piperidine

To 50 ml of diethyl ether was added a solution of 15 ml of p-tolylmagnesium bromide (1.96 M in ether). The resultant solution was cooled to 0° C. with an ice-bath and a solution of 5.3 g of 1-[3-(6-fluoro-1,2-benzisoxazol-4-yl)propyl]-4-piperidone in 50 ml of ether was added over a period of thirty mins, with stirring. The mixture was stirred at ambient temperature for two hrs, poured into 500 ml of ice-cold ammonium chloride solution, stirred for five mins and extracted with ether/ethyl acetate. The organic layer was washed with water (2×), saturated sodium chloride solution and dried over anhydrous magnesium sulfate. After filtering, the solvents were evaporated. Crystallization of the residue from ethyl ether gave 2.6 g (36%) of product, mp 96°–99° C. Recrystallization from ethyl ether gave the analytical sample, mp 98°–100° C.

Analysis

Calculated for $C_{22}H_{25}FN_2O_2$: 71.71%C, 6.84%H, 7.61%N. Found: 71.81%C, 6.85%H, 7.56%N.

EXAMPLE 7

1-[3-(6-Fluoro-1,2-benzisoxazol-3-yl)propyl]-4-hydroxy-4-(4-methoxyphenyl)piperidine hydrochloride A solution of 6.3 g of 1-[3-(6-fluoro-1,2-benzisoxazol-3-yl)propyl]-4-piperidone in 35 ml of tetrahydrofuran was slowly added to a solution of 49 ml of p-anisylmagnesium bromide (1.4 M in tetrahydrofuran). After the addition was complete, the reaction mixture was stirred at ambient temperature for one hr, diluted with ether, poured into 400 of ml saturated ammonium chloride solution and extracted with ether. The organic extracts were washed with water (2×), saturated sodium chloride solution and dried over anhydrous magnesium sulfate, filtered and concentrated. The residue was converted to 8.5 g (89%) of product, mp 100°–105° C., by treatment with ethereal hydrogen chloride. An analytical sample was obtained by recrystallization from ethyl acetate/methanol and had mp 181°–182° C. (dec).

Analysis

Calculated for $C_{22}H_{25}FN_2O_3.HCl$: 62.77%C, 6.23%H. Found: 63.04%C, 6.35%H.

EXAMPLE 8

1-[3-(6-Fluoro-1,2-benzisoxazol-3-yl)propyl]-4-hydroxy-4-(3-trifluoromethylphenyl)piperidine hydrochloride To a suspension of 1.1 g of magnesium shavings and a few drops of dibromoethane in 30 ml of ether was added a solution of 9.8 g of 3-bromobenzotrifluoride in 30 ml of ether at a rate to maintain reflux of the mixture. After the magnesium was consumed, a solution of 6 g of 1-[3-(6-Fluoro-1,2-benzisoxazol-3-yl)propyl]-4-piperidone in 500 ml of tetrahydrofuran was slowly added. After one hr, the mixture was diluted with ether, poured into 400 ml of saturated ammonium chloride solution and extracted with ether. The organic extracts were washed with water (2×), saturated sodium chloride solution and dried over anhydrous magnesium sulfate, filtered and concentrated. Treatment of the residue with ethereal hydrogen chloride gave a salt. Recrystallization from ethyl acetate/methanol gave 4 g (55%) of product, mp 214°–215° C.

Analysis

Calculated for $C_{22}H_{22}F_4N_2O_2.HCl$: 57.58%C, 5.05%H. Found: 57.48%C, 5.04%H.

EXAMPLE 9

1-[3-(6-Fluoro-1,2-benzisoxazol-3-yl)propyl]-4-hydroxy-4-(4-trifluoromethylphenyl)piperidine To a suspension of 1.2 g of magnesium shavings and a few drops of dibromoethane in 30 ml of ether was added a solution of 10.3 g of 4-bromobenzotrifluoride in 20 ml of ether at such a rate so as to maintain reflux of the mixture. After the addition was complete, the mixture was diluted with 35 ml of tetrahydrofuran, and a solution of 6.3 g of 1-[3-(6-fluoro-1,2-benzisoxazol-3-yl)propyl]-4-piperidone in 50 ml of tetrahydrofuran was slowly added. After one hr, the mixture was diluted with ether, poured into 400 ml of saturated ammonium chloride solution and extracted with ether. The organic extracts were washed with water (2×), saturated sodium chloride solution and dried over anhydrous magnesium sulfate, filtered and concentrated. Trituration with hexane/ether gave 7 g (73%) of product, mp 150°–152° C. Recrystallization from ether gave the analytical sample, mp 152°–153° C.

Analysis

Calculated for $C_{22}H_{22}F_4N_2O_2$: 62.55%C, 5.25%H, 6.63%N. Found: 62.38%C, 5.19%H, 6.84%N.

EXAMPLE 10

4-(4-Chloro-3-trifluoromethylphenyl)-1-[3-(6-fluoro-1,2-benzisoxazol-3-yl)propyl]-4-hydroxypiperidine hydrochloride To a suspension of 0.9 g of magnesium shavings and a few drops of dibromoethane in 30 ml of ether was added a solution of 9.4 g of 5-bromo-2-chlorobenzotrifluoride in 30 ml of ether at a rate to maintain reflux. After the magnesium was consumed a solution of 5 g of 1-[3-(6-fluoro-1,2-benzisoxazol-3-yl)propyl]-4-piperidone in 50 ml of tetrahydrofuran was added. After thirty mins the reaction mixture was poured into 400 ml of saturated ammonium chloride solution and extracted with ethyl acetate/ether. The organic extracts were washed with water (2×), saturated sodium chloride solution and dried over anhydrous magnesium sulfate, filtered and concentrated to an oil, which was purified by column chromatography (silic gel, tetrahydrofuran). The desired fractions were combined and concentrated to an oil, which was converted to a salt by treatment with ethereal hydrogen chloride. Recrystallization from ethyl acetate/methanol gave 3 g (34%) of product, mp 203°–204° C.

Analysis

Calculated for $C_{22}H_{21}ClF_4N_2O_2.HCl$: 53.56%C, 4.50%H. Found: 53.53%C, 4.35%H.

EXAMPLE 11

4-(4-Bromophenyl)-1-[3-(6-fluoro-1,2-benzisoxazol-3-yl)propyl]-4-hydroxypiperidine To 25 ml of ethyl ether was added 1.0 g of magnesium turnings, 0.5 ml of 1,2-dibromoethane and a few drops of a solution of 9.4 g of 1,4-dibromobenzene in 50 ml of ethyl ether. The reaction was initiated with heat and maintained by the addition of the solution of 1,4-dibromobenzene. The resultant solution was stirred at ambient temperature for fifteen mins and then a solution of 7.0 g of 1-[3-(6-fluoro-1,2-benzisoxazol-3-yl)propyl]-4-piperidone in 50 ml of tetrahydrofuran was added with vigorous stirring. After the addition was complete, the mixture was stirred at ambient temperature for thirty mins and then poured into an ice cold solution of ammonium chloride. After dilution with 200 ml of ethyl ether, the organic layer was collected, washed with water (2×), saturated sodium chloride solution and then dried over anyhydrous magnesium sulfate. After filtering, the solvents were evaporated to an oil, which was triturated with petroleum ether. The resultant precipitate was collected and dried to give 4.4 g (41%) of product, mp 138°–145° C. Recrystallization four times from ethyl ether gave the analytical sample, mp 150°–151° C.

Analysis

Calculated for $C_{21}H_{22}BrFN_2O_2$: 58.20%C, 5.12%H, 6.47%N. Found: 58.66%C, 5.20%H, 6.44%N.

We claim:

1. A compound of the formula

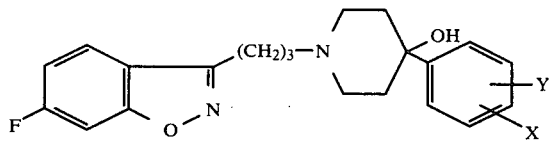

wherein X is hydrogen, loweralkyl of 1 to 5 carbon atoms, loweralkoxy of 1 to 5 carbon atoms, halogen or trifluoromethyl; Y is hydrogen or trifluoromethyl with the proviso that Y is hydrogen when X is hydrogen, loweralkyl of 1 to 5 carbon atoms, loweralkoxy of 1 to 5 carbon atoms, or trifluoromethyl and Y is hydrogen or trifluoromethyl when X is halogen; the optical antipode thereof, or pharmaceutically acceptable acid addition salt thereof.

2. A compound according to claim 1 wherein X is halogen and Y is hydrogen.

3. A compound according to claim 2 wherein the halogen is bound to the 4-position of the benzene ring.

4. The compound according to claim 1 which is 1-[3-(6-fluoro-1,2-benzisoxazol-3-yl)propyl]-4-hydroxy-4-phenylpiperidine.

5. The compound according to claim 2 which is 4-(3-chlorophenyl)-1-[3-(6-fluoro-1,2-benzisoxazol-3-yl)propyl]-4-hydroxypiperidine.

6. The compound according to claim 3 which is 4-(4-chlorophenyl)-1-[3-(6-fluoro-1,2-benzisoxazol-3-yl)propyl]-4-hydroxypiperidine.

7. The compound according to claim 3 which is 1-[3-(6-fluoro-1,2-benzisoxazol-3-yl)propyl]-4-(4-fluorophenyl)-4-hydroxypiperidine.

8. The compound according to claim 1 which is 1-[3-(6-fluoro-1,2-benzisoxazol-3-yl)propyl]-4-hydroxy-4-(2-methylphenyl)piperidine.

9. The compound according to claim 1 which is 1-[3-(6-fluoro-1,2-benzisoxazol-3-yl)propyl]-4-hydroxy-4-(4-tolyl)piperidine.

10. The compound according to claim 1 which is 1-[3-(6-fluoro-1,2-benzisoxazol-3-yl)propyl]-4-hydroxy-4-(4-methoxyphenyl)piperidine.

11. The compound according to claim 1 which is 1-[3-(6-fluoro-1,2-benzisoxazol-3-yl)propyl]-4-hydroxy-4-(3-trifluoromethylphenyl)piperidine.

12. The compound according to claim 1 which is 1-[3-(6-fluoro-1,2-benzisoxazol-3-yl)propyl]-4-hydroxy-4-(4-trifluoromethylphenyl)piperidine.

13. The compound according to claim 1 which is 4-(4-chloro-3-trifluoromethylphenyl)-1-[3-(6-fluoro-1,2-benzisoxazol-3-yl)propyl]-4-hydroxypiperidine.

14. The compound according to claim 3 which is 4-(4-bromophenyl)-1-[3-(6-fluoro-1,2-benzisoxazol-3-yl)propyl]-4-hydroxypiperidine.

* * * * *